United States Patent
Ossipov et al.

(10) Patent No.: US 10,774,164 B2
(45) Date of Patent: Sep. 15, 2020

(54) POLYMERIC COMPOSITION EXHIBITING NANOGRADIENT OF REFRACTIVE INDEX

(71) Applicant: STAAR Surgical Company, Lake Forest, CA (US)

(72) Inventors: Alexei V. Ossipov, Monrovia, CA (US); Keith Holliday, Lake Forest, CA (US)

(73) Assignee: STAAR Surgical Company, Lake Forest, CA (US)

( * ) Notice: Subject to any disclaimer, the term of this patent is extended or adjusted under 35 U.S.C. 154(b) by 0 days.

(21) Appl. No.: 16/544,567

(22) Filed: Aug. 19, 2019

(65) Prior Publication Data

US 2020/0071440 A1    Mar. 5, 2020

Related U.S. Application Data

(60) Provisional application No. 62/765,088, filed on Aug. 17, 2018.

(51) Int. Cl.
| | |
|---|---|
| *A61F 2/16* | (2006.01) |
| *B29D 11/00* | (2006.01) |
| *G02C 7/02* | (2006.01) |
| *C08F 220/28* | (2006.01) |
| *C08L 33/14* | (2006.01) |

(Continued)

(52) U.S. Cl.
CPC ............ *C08F 220/28* (2013.01); *A61L 27/24* (2013.01); *A61L 27/48* (2013.01); *A61L 27/50* (2013.01); *C08L 33/14* (2013.01); *G02B 1/041* (2013.01); *A61F 2/1627* (2013.01); *A61F 2/1645* (2015.04); *A61F 2002/1689* (2013.01); *A61F 2210/0061* (2013.01); *A61F 2250/0014* (2013.01); *A61L 2400/12* (2013.01); *B29D 11/00355* (2013.01); *C08F 220/281* (2020.02); *C08L 2203/02* (2013.01); *G02C 7/022* (2013.01); *G02C 2202/12* (2013.01)

(58) Field of Classification Search
CPC ...... A61F 2210/0061; A61F 2250/0014; A61F 2002/1696; A61F 2/15; A61F 2002/0081
See application file for complete search history.

(56) References Cited

U.S. PATENT DOCUMENTS

| | | |
|---|---|---|
| 4,199,231 A | 4/1980 | Evans |
| 4,373,225 A | 2/1983 | Eckardstein et al. |

(Continued)

FOREIGN PATENT DOCUMENTS

| | | |
|---|---|---|
| BE | 1016898 A3 | 9/2007 |
| CN | 1575146 A | 2/2005 |

(Continued)

OTHER PUBLICATIONS

Acrysof; Visual performance when it's needed most; 2 pages; retrieved from the internet (http://www.myalcon.com/products/surgical/acrysof-iq-iol/biomaterial.shtml) on Jun. 7, 2017.

(Continued)

*Primary Examiner* — David H Willse
*Assistant Examiner* — Javier G Blanco
(74) *Attorney, Agent, or Firm* — Shay Glenn LLP

(57) ABSTRACT

Ionized radiation-absorbed, dose sensitive, highly flexible polymeric compositions are provided that exhibits multidirectional changes in refractive index. Also provided are methods of producing a precision multi-directional nanogradient of refractive index in a polymeric composition.

17 Claims, 10 Drawing Sheets

(51) Int. Cl.
*A61L 27/24* (2006.01)
*A61L 27/48* (2006.01)
*A61L 27/50* (2006.01)
*G02B 1/04* (2006.01)

(56) References Cited

U.S. PATENT DOCUMENTS

| | | |
|---|---|---|
| 4,504,982 A | 3/1985 | Burk |
| 4,525,043 A | 6/1985 | Bronstein |
| 4,529,657 A | 7/1985 | Franz |
| 4,640,595 A | 2/1987 | Volk |
| 4,642,112 A | 2/1987 | Freeman |
| 4,681,102 A | 7/1987 | Bartell |
| 4,710,193 A | 12/1987 | Volk |
| 4,731,079 A | 3/1988 | Stoy |
| 4,752,123 A | 6/1988 | Blaker |
| 4,769,033 A | 9/1988 | Nordan |
| 4,787,904 A | 11/1988 | Severin et al. |
| 4,834,750 A | 5/1989 | Gupta |
| 4,981,342 A | 1/1991 | Fiala |
| 4,990,582 A | 2/1991 | Salamone |
| 5,000,676 A | 3/1991 | Fiala |
| 5,019,098 A | 5/1991 | Mercier |
| 5,044,742 A | 9/1991 | Cohen |
| 5,073,021 A | 12/1991 | Marron |
| 5,142,411 A | 8/1992 | Fiala |
| 5,161,964 A | 11/1992 | Frigiere et al. |
| 5,198,844 A | 3/1993 | Roffman et al. |
| 5,217,491 A | 6/1993 | Vanderbilt |
| 5,245,366 A | 9/1993 | Svochak |
| 5,260,727 A | 11/1993 | Oksman et al. |
| 5,286,829 A | 2/1994 | Fedorov et al. |
| 5,290,892 A | 3/1994 | Namdaran et al. |
| 5,329,363 A | 7/1994 | Moskovich |
| 5,331,027 A | 7/1994 | Whitbourne |
| 5,349,396 A | 9/1994 | Roffman et al. |
| 5,359,021 A | 10/1994 | Weinschenk et al. |
| 5,410,375 A | 4/1995 | Fiala |
| 5,436,678 A | 7/1995 | Carroll |
| 5,437,647 A | 8/1995 | Firth et al. |
| 5,480,428 A | 1/1996 | Fedorov et al. |
| 5,485,228 A | 1/1996 | Roffman et al. |
| 5,494,484 A | 2/1996 | Feingold |
| 5,499,987 A | 3/1996 | Feingold |
| 5,517,260 A | 5/1996 | Glady et al. |
| 5,523,316 A | 6/1996 | Gan et al. |
| 5,574,518 A | 11/1996 | Mercure |
| 5,603,774 A | 2/1997 | LeBoeuf et al. |
| 5,616,148 A | 4/1997 | Eagles et al. |
| 5,620,450 A | 4/1997 | Eagles et al. |
| 5,654,349 A | 8/1997 | Feingold et al. |
| 5,654,363 A | 8/1997 | Feingold et al. |
| 5,654,388 A | 8/1997 | Feingold et al. |
| 5,661,218 A | 8/1997 | Feingold et al. |
| 5,674,282 A | 10/1997 | Cumming |
| 5,684,560 A | 11/1997 | Roffman et al. |
| 5,693,095 A | 12/1997 | Freeman et al. |
| 5,715,031 A | 2/1998 | Roffman et al. |
| 5,716,364 A | 2/1998 | Makker et al. |
| 5,766,245 A | 6/1998 | Fedorov et al. |
| 5,771,088 A | 6/1998 | Perrott |
| 5,796,462 A | 8/1998 | Roffman et al. |
| 5,800,532 A | 9/1998 | Lieberman |
| 5,814,680 A | 9/1998 | Imafuku et al. |
| 5,822,091 A | 10/1998 | Baker |
| 5,843,186 A | 12/1998 | Christ |
| 5,847,802 A | 12/1998 | Menezes et al. |
| 5,856,120 A | 1/1999 | Fedorov et al. |
| 5,864,378 A | 1/1999 | Portney |
| 5,882,421 A | 3/1999 | LeBoeuf et al. |
| 5,910,537 A | 6/1999 | Feingold et al. |
| 5,913,989 A | 6/1999 | Wycliffe et al. |
| 5,922,821 A | 7/1999 | LeBoeuf et al. |
| 5,929,969 A | 7/1999 | Roffman |
| 5,947,975 A | 9/1999 | Kikuchi et al. |
| 5,982,543 A | 11/1999 | Fiala |
| 6,036,891 A | 3/2000 | Liao et al. |
| 6,045,578 A | 4/2000 | Collins et al. |
| 6,106,553 A | 8/2000 | Feingold |
| 6,110,202 A | 8/2000 | Barraquer et al. |
| 6,120,148 A | 9/2000 | Fiala et al. |
| 6,148,862 A | 11/2000 | Doll |
| 6,150,472 A | 11/2000 | Engbers |
| 6,165,490 A | 12/2000 | Fedorov et al. |
| 6,179,420 B1 | 1/2001 | Roffman et al. |
| 6,203,973 B1 | 3/2001 | Chen et al. |
| 6,238,975 B1 | 5/2001 | Fliesler et al. |
| 6,241,766 B1 | 6/2001 | Liao et al. |
| 6,244,709 B1 | 6/2001 | Vayntraub et al. |
| 6,245,106 B1 | 6/2001 | Makker et al. |
| 6,271,281 B1 | 8/2001 | Liao et al. |
| 6,386,357 B1 | 5/2002 | Egawa |
| 6,398,809 B1 | 6/2002 | Hoffmann et al. |
| 6,457,826 B1 | 10/2002 | Lett |
| 6,488,708 B2 | 12/2002 | Sarfarazi |
| 6,500,181 B1 | 12/2002 | Portney |
| 6,506,212 B2 | 1/2003 | Zhou et al. |
| 6,520,638 B1 | 2/2003 | Roffman et al. |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,557,998 B2 | 5/2003 | Portney |
| 6,576,011 B2 | 6/2003 | Portney |
| 6,576,012 B2 | 6/2003 | Lang |
| 6,609,793 B2 | 8/2003 | Norrby et al. |
| 6,709,103 B1 | 3/2004 | Roffman et al. |
| 6,737,448 B2 | 5/2004 | Liao |
| 6,790,232 B1 | 9/2004 | Lang |
| 6,802,606 B2 | 10/2004 | Roffman et al. |
| 6,899,425 B2 | 5/2005 | Roffman et al. |
| 6,923,539 B2 | 8/2005 | Simpson et al. |
| 6,957,891 B2 | 10/2005 | Fiala |
| 7,036,931 B2 | 5/2006 | Lindacher et al. |
| 7,057,816 B1 | 6/2006 | Allen et al. |
| 7,061,693 B2 | 6/2006 | Zalevsky |
| 7,073,906 B1 | 7/2006 | Portney |
| 7,118,214 B2 | 10/2006 | Cox |
| 7,157,538 B2 | 1/2007 | Callaghan et al. |
| 7,178,918 B2 | 2/2007 | Griffin |
| 7,261,412 B2 | 8/2007 | Somani et al. |
| 7,789,910 B2 | 9/2010 | Knox et al. |
| 7,828,431 B2 | 11/2010 | Ho et al. |
| 7,871,162 B2 | 1/2011 | Weeber |
| 7,997,727 B2 | 8/2011 | Ho et al. |
| 8,231,219 B2 | 7/2012 | Weeber |
| 8,485,662 B2 | 7/2013 | Collins et al. |
| 8,486,055 B2 | 7/2013 | Knox et al. |
| 8,580,228 B2 | 11/2013 | Zones et al. |
| 8,617,147 B2 | 12/2013 | Knox et al. |
| 8,740,978 B2 | 6/2014 | Weeber et al. |
| 8,747,466 B2 | 6/2014 | Weeber et al. |
| 8,862,447 B2 | 10/2014 | Weeber |
| 8,894,204 B2 | 11/2014 | Weeber et al. |
| 8,911,086 B2 | 12/2014 | Dai |
| 8,974,526 B2 | 3/2015 | Bogaert |
| 9,060,847 B2 | 6/2015 | Smith et al. |
| 9,144,491 B2 | 9/2015 | Knox et al. |
| 9,195,074 B2 | 11/2015 | Bakaraju et al. |
| 9,201,250 B2 | 12/2015 | Bakaraju et al. |
| 9,216,080 B2 | 12/2015 | Bogaert et al. |
| 9,220,591 B2 | 12/2015 | Zhao |
| RE45,969 E | 4/2016 | Hong et al. |
| 9,301,833 B2 | 4/2016 | Gulati et al. |
| 9,329,408 B2 | 5/2016 | Matsunaga et al. |
| 9,535,263 B2 | 1/2017 | Bakaraju et al. |
| 9,545,340 B1 | 1/2017 | Knox et al. |
| 9,557,579 B2 | 1/2017 | Lindacher et al. |
| 9,636,216 B2 | 5/2017 | Ossipov et al. |
| 9,690,882 B2 | 6/2017 | Dobschal |
| 9,717,628 B2 | 8/2017 | Vidal Canovas et al. |
| 9,823,493 B2 | 11/2017 | Caldarise et al. |
| 10,117,775 B2 | 11/2018 | Gulati et al. |
| 2001/0044657 A1 | 11/2001 | Kellan |

(56) References Cited

U.S. PATENT DOCUMENTS

| | | |
|---|---|---|
| 2002/0120330 A1 | 8/2002 | Galin |
| 2003/0014107 A1 | 1/2003 | Reynard |
| 2003/0063254 A1 | 4/2003 | Piers et al. |
| 2003/0081171 A1 | 5/2003 | Griffin |
| 2003/0103187 A1 | 6/2003 | Miyamura et al. |
| 2003/0187505 A1 | 10/2003 | Liao |
| 2004/0087963 A1 | 5/2004 | Ossipov et al. |
| 2005/0125000 A1 | 6/2005 | Tourrette et al. |
| 2005/0147735 A1 | 7/2005 | Lowery et al. |
| 2005/0182419 A1 | 8/2005 | Tsai |
| 2005/0259222 A1 | 11/2005 | Kelch et al. |
| 2006/0089712 A1 | 4/2006 | Malecaze |
| 2006/0095127 A1 | 5/2006 | Feingold et al. |
| 2006/0098162 A1 | 5/2006 | Bandhauer et al. |
| 2006/0098163 A1 | 5/2006 | Bandhauer et al. |
| 2006/0116763 A1 | 6/2006 | Simpson |
| 2006/0167545 A1 | 7/2006 | Fiala et al. |
| 2006/0176572 A1 | 8/2006 | Fiala |
| 2006/0187413 A1 | 8/2006 | Applegate et al. |
| 2006/0200167 A1 | 9/2006 | Peterson et al. |
| 2006/0244904 A1 | 11/2006 | Hong et al. |
| 2006/0244906 A1 | 11/2006 | Piers et al. |
| 2007/0000801 A1 | 1/2007 | Mauran et al. |
| 2007/0168028 A1 | 7/2007 | Tran et al. |
| 2007/0258143 A1 | 11/2007 | Portney |
| 2008/0013043 A1 | 1/2008 | Ye et al. |
| 2008/0086208 A1 | 4/2008 | Nordan |
| 2008/0114373 A1 | 5/2008 | Rathert |
| 2008/0225409 A1 | 9/2008 | Alexay |
| 2009/0059163 A1 | 3/2009 | Pinto |
| 2009/0112313 A1 | 4/2009 | Mentak |
| 2009/0157179 A1 | 6/2009 | Pinto et al. |
| 2009/0210054 A1 | 8/2009 | Weeber et al. |
| 2009/0279048 A1 | 11/2009 | Hong et al. |
| 2010/0079723 A1 | 4/2010 | Kingston et al. |
| 2010/0087921 A1 | 4/2010 | Simpson |
| 2010/0125279 A1 | 5/2010 | Karakelle et al. |
| 2010/0131059 A1 | 5/2010 | Callahan et al. |
| 2010/0161051 A1 | 6/2010 | Hong |
| 2010/0188636 A1 | 7/2010 | Pinto et al. |
| 2011/0046634 A1 | 2/2011 | Rathert |
| 2011/0218623 A1 | 9/2011 | Dishler et al. |
| 2011/0313519 A1 | 12/2011 | Cumming |
| 2011/0313525 A1 | 12/2011 | Cumming |
| 2012/0071888 A1 | 3/2012 | Putallaz et al. |
| 2013/0090730 A1 | 4/2013 | Weeber et al. |
| 2013/0226294 A1 | 8/2013 | Van Der Mooren et al. |
| 2014/0022508 A1 | 1/2014 | Ben-Yaish et al. |
| 2014/0135919 A1 | 5/2014 | Gontijo et al. |
| 2014/0200588 A1 | 7/2014 | Anderson et al. |
| 2016/0067035 A1 | 3/2016 | Gontijo et al. |
| 2016/0116764 A1 | 4/2016 | Newman |
| 2016/0193037 A1 | 7/2016 | Pinto et al. |
| 2016/0198942 A1 | 7/2016 | Dai |
| 2016/0302916 A1 | 10/2016 | Sarver et al. |
| 2016/0320633 A1 | 11/2016 | Weeber |
| 2016/0324629 A1 | 11/2016 | Sandstedt et al. |
| 2016/0346076 A1 | 12/2016 | Paul et al. |
| 2017/0196682 A1 | 7/2017 | Lawu |
| 2017/0245983 A1 | 8/2017 | Hong et al. |
| 2017/0245987 A1 | 8/2017 | Canovas Vidal et al. |
| 2017/0258577 A1 | 9/2017 | Pinto et al. |
| 2017/0276963 A1 | 9/2017 | Brennan et al. |
| 2017/0290657 A1 | 10/2017 | Luque |
| 2017/0319332 A1 | 11/2017 | Kahook et al. |
| 2017/0325937 A1 | 11/2017 | Weeber et al. |
| 2018/0231696 A1 | 8/2018 | Knox et al. |
| 2018/0318064 A1 | 11/2018 | Paul et al. |
| 2019/0076242 A1 | 3/2019 | Pinto |

FOREIGN PATENT DOCUMENTS

| | | |
|---|---|---|
| CN | 1671336 A | 9/2005 |
| CN | 1835719 A | 9/2006 |
| CN | 1845712 A | 10/2006 |
| CN | 101073519 A | 11/2007 |
| CN | 101199437 A | 6/2008 |
| CN | 101252895 A | 8/2008 |
| CN | 101437468 A | 5/2009 |
| CN | 101490600 A | 7/2009 |
| CN | 101796451 A | 8/2010 |
| CN | 102106764 A | 6/2011 |
| CN | 202086618 U | 12/2011 |
| EP | 470811 A2 | 2/1992 |
| EP | 485197 A1 | 5/1992 |
| EP | 503111 A1 | 9/1992 |
| EP | 1402852 A1 | 3/2004 |
| EP | 1424049 A1 | 6/2004 |
| EP | 1862148 A1 | 12/2007 |
| EP | 1958593 A1 | 8/2008 |
| JP | 63-310820 A | 12/1988 |
| JP | 64-002644 A | 1/1989 |
| JP | H07-184989 A | 7/1995 |
| JP | 2005002377 A | 1/2005 |
| JP | 2005523981 A | 8/2005 |
| JP | 2006522674 A | 10/2006 |
| JP | 2005062965 A | 6/2007 |
| JP | 2007536047 A | 12/2007 |
| JP | 2009525835 A | 7/2009 |
| JP | 2009528855 A | 8/2009 |
| JP | 2012517029 A | 7/2012 |
| KR | 101030689 B1 | 4/2011 |
| KR | 10-1248488 B1 | 4/2013 |
| WO | WO94/07436 A1 | 4/1994 |
| WO | WO94/013225 A1 | 6/1994 |
| WO | WO94/025510 A1 | 11/1994 |
| WO | WO96/040303 A1 | 12/1996 |
| WO | WO97/35896 A1 | 10/1997 |
| WO | WO98/003894 A1 | 1/1998 |
| WO | WO99/057720 A1 | 11/1999 |
| WO | WO01/010354 A1 | 2/2001 |
| WO | WO01/071392 A1 | 9/2001 |
| WO | WO01/089424 A1 | 11/2001 |
| WO | WO02/051338 A1 | 7/2002 |
| WO | WO03/101355 A1 | 12/2003 |
| WO | WO2004/095187 A2 | 11/2004 |
| WO | WO2005/046527 A2 | 5/2005 |
| WO | WO2005/099630 A1 | 10/2005 |
| WO | WO2006/014624 A2 | 2/2006 |
| WO | WO2006/056847 A1 | 6/2006 |
| WO | WO2006/100086 A1 | 9/2006 |
| WO | WO2006/108005 A2 | 10/2006 |
| WO | WO2007/137100 A2 | 11/2007 |
| WO | WO2008/065573 A1 | 6/2008 |
| WO | WO2008/077006 A1 | 6/2008 |
| WO | WO2008/080464 A1 | 7/2008 |
| WO | WO2009/029481 A1 | 3/2009 |
| WO | WO2009/130610 A2 | 10/2009 |
| WO | WO2010/100523 A1 | 9/2010 |
| WO | WO2010/135685 A1 | 11/2010 |
| WO | WO2011/153158 A1 | 12/2011 |
| WO | WO2012/015300 A1 | 2/2012 |
| WO | WO2012/083143 A1 | 6/2012 |
| WO | WO2013/028992 A1 | 2/2013 |
| WO | WO2013/159045 A1 | 10/2013 |
| WO | WO2016/025315 A1 | 2/2016 |
| WO | WO2016/040331 A1 | 3/2016 |
| WO | WO2016/145068 A1 | 9/2016 |
| WO | WO2017/156077 A1 | 9/2017 |

OTHER PUBLICATIONS

Altissimo; E-beam lithography for micro-nanofabrication; Biomicrofluidics; 4(2); 026503; doi: 10.1063/1.3437589; 6 pages; Jun. 15, 2010.

answers.com; Spherochromatism (definition); 1 page; retrieved from the internet (Answers.com) on Feb. 26, 2009.

Atchison; Design of aspheric intraocular lenses; Ophthalmic and Physiological Optics; 11(2); pp. 137-146; Apr. 1991.

Christensen; Bernard schmidt: His camera and its derivatives; 4 pages; retrieved from the internet (www.fvastro.org/articles/schmidtp2.htm) on Feb. 26, 2009.

(56) References Cited

OTHER PUBLICATIONS

Flat Schmidt Camera: 5 pages; retrieved from the internet (www.5f.biglobe.ne.jp/-kztanaka/flatschmidtcamera.html) on Feb. 26, 2009.
Freeman; An introduction to chromatic aberration in refractors; 4 pages; retrieved from the internet (www.maa.mhn.de/scholar/chromatic_aberration.html); on Feb. 26, 2009.
Greenwall; Glass versus polycarbonate; 3 pages; retrieved from the internet (http://www.greenwallsolutions.com/installation/glass-vs-polycarbonate/) on Oct. 2012.
Liou et al.; Anatomically accurate, finite model eye for optical modeling; Journal of the Optical Society of America, Optical Society of America (US), 14(8); pp. 1684-1695; Aug. 1997.
Malyugin et al.; Gradient refractive index optics IOL: theroretical background and clinical results; Middle East African Journal of Ophthalmology; 21(1); pp. 32-39; 22 pages (Author Manuscript); Jan. 2014.
Ophthalmo Pharma; Solo Pre-Loaded IOL Injector; 11 pages; Jul. 2010.
PFAFF; Guide to making schmidt correctors; 6 pages; retrieved from the internet (www.considine.net/drowesmi/pfaff/pfaff.htm) on Feb. 26, 2009.
Smith; Improving a design; Modern Lens Design: A Resource Manual; Genesee Optics Software, Inc.; Rochester, New York; pp. 291-295; (year of pub. sufficiently earlier than effective US filing date and any foreign priority date) 1992.
Smith; Sec. 12.5, Archromatic Objectives (Design Forms); Modern Optical Engineering: The design of optical systems, Second Edition; McGraw-Hill; Chapter 3, pp. 375-384; (year of pub. sufficiently earlier than effective US filing date and any foreign priority date) 1990.
Smith; Sec. 3.7, Aberration Correction and Residuals; Modern Optical Engineering: The design of optical systems, Second Edition; McGraw-Hill; Chapter Twelve, pp. 76-79; (year of pub. sufficiently earlier than effective US filing date and any foreign priority date) 1990.
Southall; Objective of microscope; Mirrors, Prisms and Lenses: A Text-Book of Geometrical Optics; 3rd Edition; The MacMillian Company; pp. 675-677; (year of pub. sufficiently earlier than effective US filing date and any foreign priority date) 1933.
Staar Surgical Company; Bank of America Merrill Lynch Health Care Conference; 19 pages; May 16, 2018.
Telescope Optic.Net; Full-aperture schmidt corrector: Schmidt camera; 3 pages; retrieved from the internet (www.telescope-optics.net/Schmidt-camera.htm) on Feb. 26, 2009.
Telescope Optic.Net; Secondary spectrum and spherochromatism; 3 pages; retrieved from the internet (www.telescope-optics.net/secondaryspectrum_spherochromatism.html) on Feb. 26, 2009.
Thibos: Retinal image quality and visual performance; Wavefront Congress Short Course; Indiana University, School of Optometry; 40 pages; Feb. 2008.
Wikipedia; Schmidt camera; 2 pages; retrieved from the internet (en.wikipedia.org/wiki/Schmidt_camera) on Feb. 26, 2009.
Ossipov et al.; U.S. Appl. No. 15/583,758 entitled "Injector cartridge with improved lubricity," filed May 1, 2017.

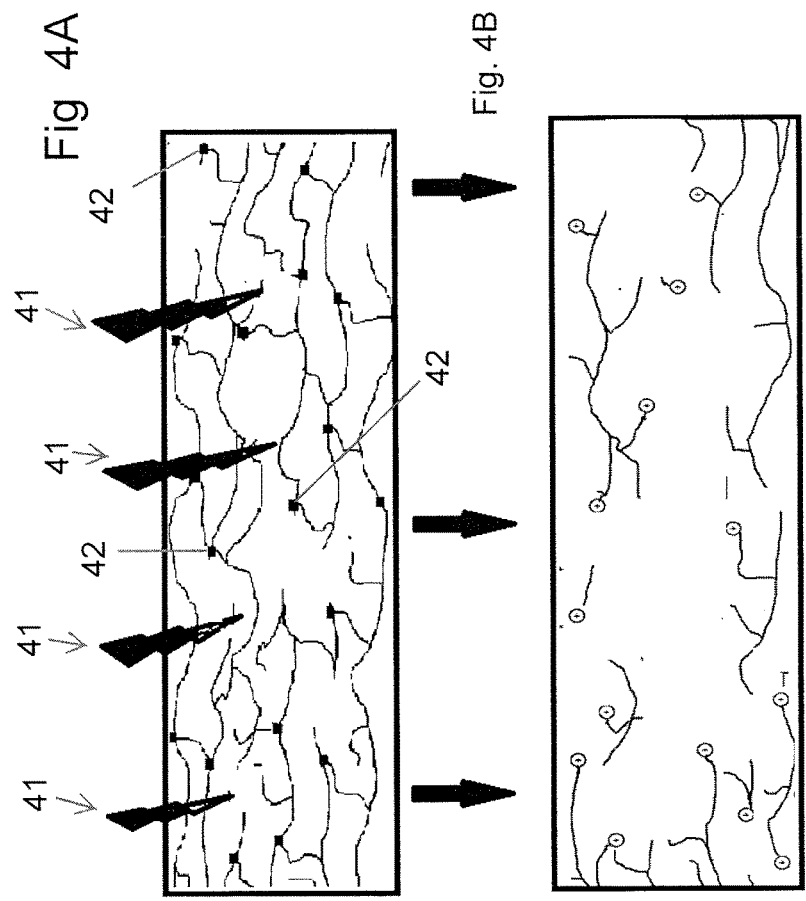
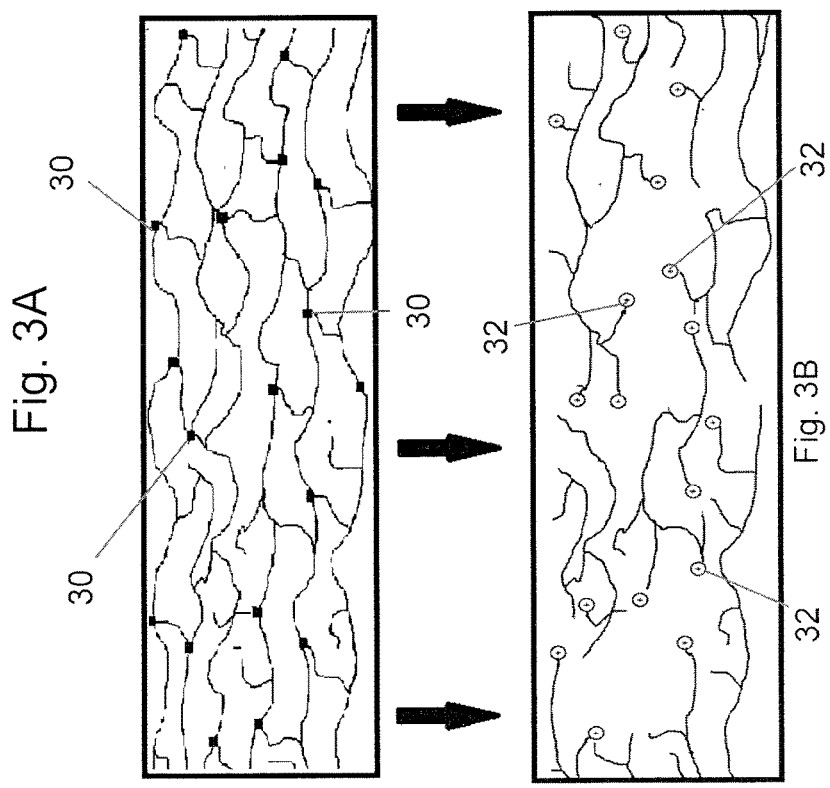

Decrease in chain intermolecular forces (due to repulsion) = increase in swelling $$M^{2+} = Mg^{2+}, Ca^{2+}$$

⦃ = random fragments of copolymer chains

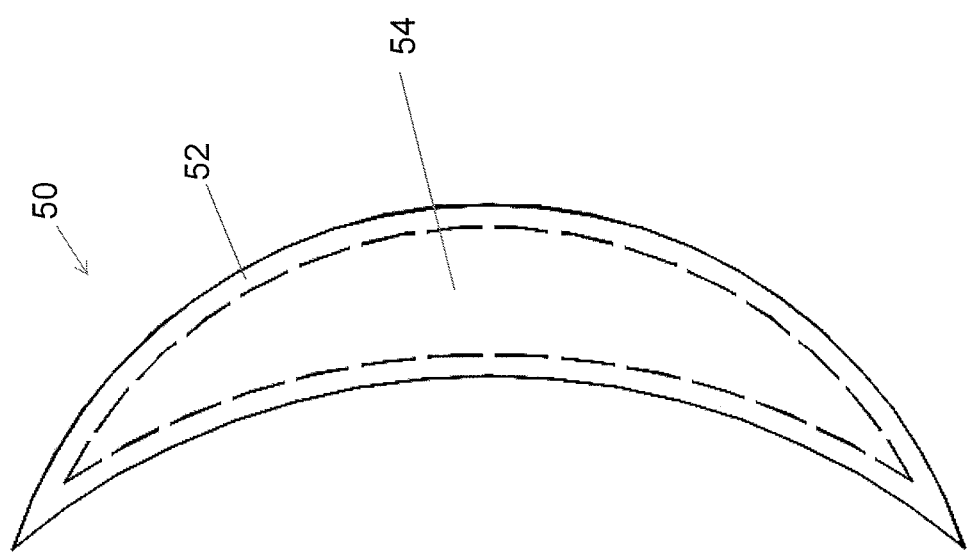

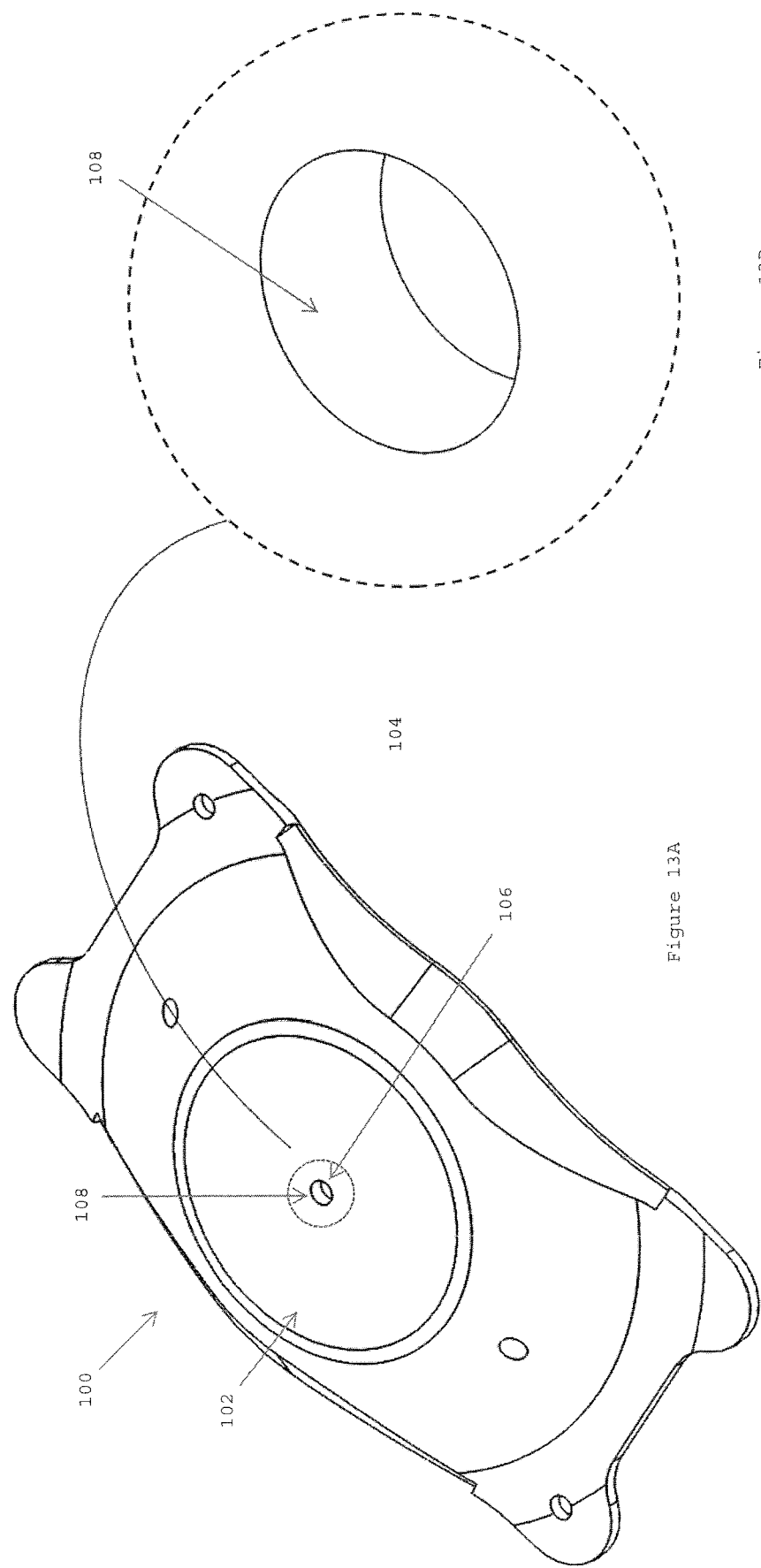

POLYMERIC COMPOSITION EXHIBITING NANOGRADIENT OF REFRACTIVE INDEX

CROSS REFERENCE TO RELATED APPLICATIONS

This application claims the benefit of U.S. Provisional Application No. 62/765,088, filed Aug. 17, 2018, which is incorporated by reference herein for all purposes.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

An ionized radiation-absorbed, dose sensitive, highly flexible polymeric composition is provided that exhibits multidirectional changes in refractive index. Also provided is a method of producing a precision multi-directional gradient of refractive index in a polymeric composition.

BACKGROUND

A lens that has a refractive index that varies in a controlled way throughout its body is referred to as a gradient refractive index (GRIN) lens. The refractive index typically changes as a gradient, in that it varies gradually throughout the body of the lens. The naturally occurring human crystalline lens is an example of a lens having a gradient of refractive index.

Production of a single piece foldable multifocal gradient intraocular lens (IOL) has been reported wherein the IOL was manufactured with step-by-step polymerization technology in transfer molds of photohardening material (ultraviolet light) with various refraction indices (oligourethanmethacrylate). See Malyugin et al., Middle East Afr. J. Ophthalmol. 2014 January-March; 21(1): 32-39. This technology can produce multifocal artificial lenses with gradient optics. However, the manufacturing process combines stages of material polymerization with lens manufacturing concurrently.

SUMMARY OF THE DISCLOSURE

Methodology for forming GRIN IOLs is desirable, in that optical parameters, such as image quality, focal length, and depth of focus, can be defined for the manufactured lens by controlling the variation in refractive index. This methodology enables ophthalmic lenses (e.g., IOLs) to be manufactured to specification for a particular patient's vision correction requirements. Methodology that enables refractive index modification of a previously manufactured ophthalmic lens would be desirable, as would methodology for preparation of GRIN lenses for applications other than intraocular use.

One aspect of the disclosure is a lens, optionally an ophthalmic lens, including an optic body made from a copolymer having a three-dimensional polymeric matrix, wherein the three dimensional polymeric matrix of the copolymer has a non-uniform cross-link density.

The three dimensional polymeric matrix may include a first region with fewer cross links than a second region.

The first region and the second region may be within a gradient of cross-link density. The three dimensional polymeric matrix may further include a third region that is not within the gradient, the third region including a layer having a uniform cross-link density. The first region may be closer to a periphery of the optic body than the second region.

The first region may be a first layer with a first cross-link density, and the second region may be a second layer with a second cross-link density. The first region may be a surface layer of the optic body, the first region having fewer cross-links than the second region.

The first region may be closer to a periphery of the optic body.

The entire optic body may have a gradient cross-link density.

The three-dimensional polymeric matrix may have a refractive index distribution substantially the same as a refractive index distribution of a natural crystalline lens.

A shape of the optic body may be substantially the same as a shape of a natural crystalline lens.

The entire optic body may not have a gradient cross-link density.

The optic body may be a toric lens.

The copolymer may include at least one non-ionic acrylic monomer and at least one ionic monomer. The copolymer may further comprise a collagen material. The ionic monomer may be an organic acid. A weight ratio of the non-ionic acrylic monomer to the ionic monomer may be 10:1 to 10,000:1, such as 50:1 to 200:1, such as 75:1 to 175:1, such as 75:1, 100:1, 125:1, 150:1, or 175:1. The non-ionic acrylic monomer may be hydroxyethylmethacrylate.

The non-uniform crosslink density of the matrix may be adapted to create an anti-reflection surface layer in the optic body when the optic body is exposed to aqueous in an eye. An anti-reflection layer may comprise a region of the matrix that is 50 nm to 400 nm thick. The anti-reflection layer may comprise a region of the matrix that is 0.1 micron to 10 microns thick. The anti-reflection layer may comprise a region of the matrix that is 1 micron to 100 microns thick. The anti-reflection surface layer may be at least partially disposed around a central aperture formed in the optic body.

The optic body may be an optic body of an IOL.

The three-dimensional matrix may be dimensionally stable through steam sterilization as part of a "wet pack" and is hydrolytically stable during long term use.

The non-uniform cross-link density may adapt the optic body, when placed in an eye and exposed to aqueous, to focus light from a wide range of distances without moving or changing shape, optionally with a vergence of 0 to 3 D, optionally 0 to 2.5 D, optionally 0 to 2 D, optionally 0 to 1.5 D, optionally 0 to 1.0 D.

The non-uniform cross-link density may adapt the optic body, when placed in an eye and exposed to aqueous, to correct for astigmatism.

The three dimensional polymeric matrix may have a lower cross-link density near a surface of the optic body than in a region further inward relative to the surface.

The lens may further comprise a non-optic body portion (e.g., one or more haptics), and wherein the non-optic body portion includes a non-optic three-dimensional polymeric matrix, wherein the non-optic three dimensional polymeric matrix has a non-uniform cross-link density.

The lens may further comprise a hydrating solution to which the optic body has been exposed, wherein the non-uniform cross-link density causes the three-dimensional polymeric matrix to swell in a non-uniform manner when hydrated in the solution, thereby creating a non-uniform refractive index within the optic body.

The hydrating solution may be a balanced salt solution.

The hydrating solution may include constituent parts such that when the lens is exposed to aqueous humor in an eye, the amount of swelling in the three-dimensional polymeric matrix will not substantially change. The hydrating solution may be a balanced salt solution.

The hydrating solution may include constituent parts such that when the lens is exposed to aqueous humor in an eye, the amount of swelling in the three-dimensional polymeric matrix increases. The hydrating solution may be a sodium chloride solution.

The hydrating solution may include constituent parts such that when the lens is exposed to aqueous humor in an eye, the amount of swelling in the three-dimensional polymeric matrix decreases.

The hydrating solution may include at least one of magnesium ions or calcium ions.

The non-uniform refractive index may include first and second discrete layers having first and second refractive indices, respectively. The non-uniform cross-link density may further include a gradient cross-link density.

One aspect of the disclosure is a method of placing any of the lenses herein in a hydrating solution, wherein placing the lens in the hydrating solution causes a non-uniform swelling of the matrix, thereby creating a non-uniform refractive index in the optic body. The method may include placing the lens in a balanced salt solution.

One aspect of the disclosure is a method of implanting any of the lenses herein, wherein the method of implanting causes a change in the swelling in the matrix. Implanting may cause the matrix to swell more in at least a portion of the matrix. Implanting may cause a decrease in swelling in at least a portion of the matrix. Implanting the lens may cause the lens to increase in overall volume to an implanted configuration.

One aspect of the disclosure is a method of implanting any of the lenses herein, wherein the method of implanting does not causes a substantial change in the swelling in the matrix.

One aspect of the disclosure is a method of implanting any of the lenses herein, wherein implanting the lens comprises inserting the lens through a delivery device in a state in which the lens has a smaller volume than a lens volume in a fully hydrated, implanted state.

One aspect of the disclosure is a method for inducing a refractive index gradient in a three-dimensional polymeric matrix, the method including providing a formed body (e.g., already cured) having a three-dimensional polymeric matrix comprising a copolymer system prepared from at least one non-ionic acrylic monomer and at least one ionic monomer; and irradiating the three-dimensional polymeric matrix with ionizing energy in a pattern configured to thereby create a non-uniform cross-link density within the matrix.

The method can be used in combination with any of the lenses herein.

The ionizing energy may be electron beams. The ionizing energy may be x-rays.

The method may further include maintaining the body in a stationary position, and wherein irradiating comprises moving an ionizing energy source in at least one direction. The method may include maintaining an ionizing energy source in a stationary position, and moving the body in at least one direction during the irradiating step. The method may include moving both the body and the energy source, simultaneously or serially, or any combination thereof.

The irradiating step may create a gradient of cross-link density in at least a portion of the matrix.

The irradiating step may create a gradient of cross-link density in substantially the entire matrix.

The irradiating step may create a first layer with a first cross-link density less than a cross-link density of a second region the matrix. The first layer may be a surface layer of the body.

The copolymer system may further comprise a collagen material.

The ionic monomer may be an organic acid.

The at least one non-ionic acrylic monomer may be hydroxyethylmethacrylate, and wherein the at least one ionic monomer may be an acrylic monomer.

The body may be an optic body of an intraocular lens.

The irradiated three-dimensional polymeric matrix may be dimensionally stable through steam sterilization as part of a "wet pack" and may be hydrolytically stable during long term use.

The irradiating step may create a surface anti-reflective layer, optionally from 50 nm to 400 nm thick, optionally from 0.1 microns to 10 microns thick, or optionally from 1 micron to 100 microns thick.

The irradiating step may create a non-uniform cross-link density such that, when the body is hydrated in aqueous in an eye, the body is adapted to focus light from a wide range of distances without moving or changing shape, optionally with a vergence of 0 to 3 D, optionally 0 to 2.5D, optionally 0 to 2D, optionally 0 to 1.5 D.

The irradiating step can be initiated after one or more peripheral support (e.g., haptics) have already been formed integrally with the formed body.

The ionizing energy may be X-rays.

BRIEF DESCRIPTION OF THE DRAWINGS

FIG. 3A illustrates a formed (e.g., cured) polymeric material with crosslinks.

FIG. 3B illustrates the formed polymeric material from FIG. 3A after being hydrated in solution, which causes swelling.

FIG. 4A illustrates a formed polymeric material after exposure to ionizing energy.

FIG. 4B illustrates the polymeric material from FIG. 4A after being hydrated in solution, which causes swelling. More swelling has occurred in FIG. 4B than in FIG. 3B.

FIG. 6 illustrates an exemplary lens with a thin anti-reflection layer formed therein, including a main lens body portion.

FIG. 13A illustrates an exemplary lens that may be irradiated using the methods herein, the lens including one or more apertures in the optic.

FIG. 13B illustrates a central aperture of an optic body and a region around the aperture that may be irradiated using methods herein to create an anti-reflection layer at the location of the aperture.

DETAILED DESCRIPTION OF THE DISCLOSURE

Figure 1:
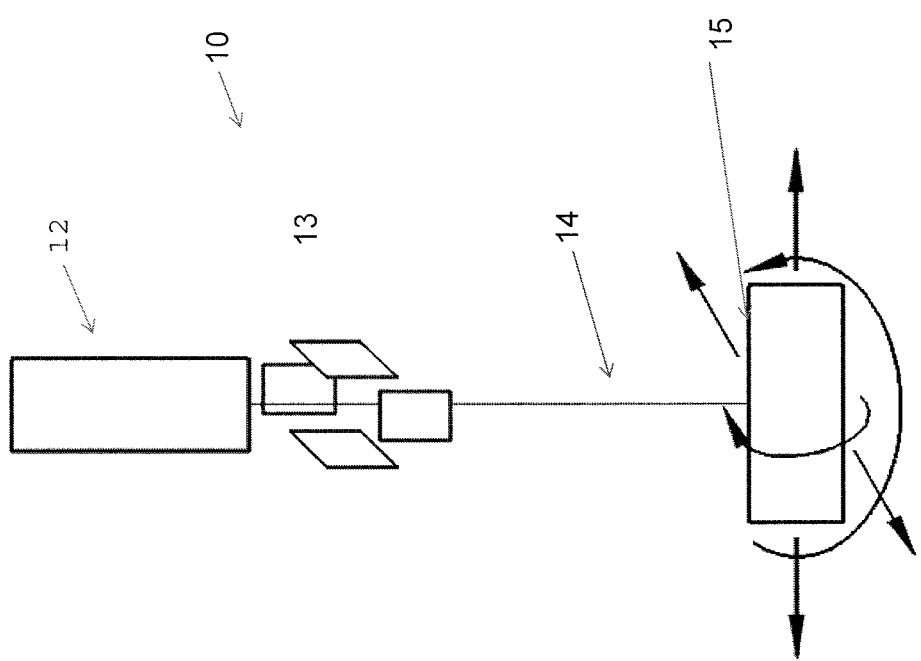
FIG. 1 is an exemplary system for applying ionizing energy to a polymeric body.

One aspect of the disclosure includes lenses (e.g., ophthalmic lenses) that have been manufactured with a refractive index ("RI") that varies in a controlled way throughout their lens bodies. In some instances the RI varies in only a portion of the lens body. In some instances the varying RI may be a gradient RI, while in some examples it may refer generally to one or more layers of the body each having a different RI. The lenses herein may include one or more body regions having a gradient RI, as well as one or more body regions having a uniform RI, and any combination thereof.

One aspect of this disclosure is related to methods of creating the varying RI in the lens.

In general, the methods of creating the variable RI in the lens body (which may be referred to herein as an optic body) occur after the body of the material has been formed, i.e., after curing one or more monomers to form a cured body of polymeric material. This is in contrast to alternative approaches that may create a varying RI during the process of forming the body.

The methods herein that create the varying RI may take place after one or more optic surfaces have already been formed in an optic body (e.g., via lathing to create the one or more optic surfaces). Alternatively, the methods that create the varying RI may occur prior to forming one or more optic surfaces of an optic body. For example, the methods may occur prior to an anterior and/or a posterior surface of an optic body being formed (e.g., lathing). In these alternative examples, the methods may be performed on, for example, a cured body of polymeric material (e.g., a cylindrical button), after which one or more optical surfaces may then be formed thereon.

An exemplary advantage of the methods described herein is it can be used on a wide variety of optic bodies that have been formed using known curing techniques. This allows for existing techniques to be used to form a body of material (e.g., curing), after which the methods herein can be utilized to modify the RI in one or more regions of the lens in a very controlled manner to treat a wide variety of optical disorders (e.g., astigmatism) or to modify the lens in other ways to create a desired optical effect (e.g., creating an anti-reflective surface layer in an outermost region of the lens).

The term "refractive index" ("RI") herein encompasses a measurement of the degree of refraction in translucent/transparent substances, especially the ocular media. The RI is measured as the relative velocity of light in another medium (such as a polymeric material) as compared to the velocity of light in vacuum. For example, the RI (n) of water is 1.33.

Any of the lenses herein may have one or more regions that have a gradient RI. Any of the lenses herein may have one or more regions that interface where there is an abrupt change in RI between the regions. Any of the lenses herein may have one or more regions that have a constant RI. Any of the lenses herein may include any combination of the exemplary regions set forth in this paragraph. Any of the methods of use herein may be utilized to create any of the lenses set forth in this paragraph.

The natural human crystalline lens is a gradient refractive index lens (GRIN) and the RI typically changes as a gradient, in that it varies gradually throughout the body of the lens. As an example, the methods herein can facilitate the manufacture of lenses that have similar performance to the crystalline lens of the eye by defining optical parameters, such as image quality, focal length, and depth of focus, by controlling the variation in refractive index, and the manufactured lenses are GRIN lenses. However, in some lenses, it may be advantageous to provide an artificial lens that has one or more abrupt changes in RI instead, or in addition to, a gradient. Portions of the lens may also have a constant RI.

The disclosure herein includes methods of creating desired RI profiles within an already-formed lens. The techniques herein apply ionizing energy in a particular pattern or manner to a formed polymeric material, and in some instances the ionizing energy may be electron beams. The electron beams (or other ionizing energy) cause bonds to break in the formed polymeric material. Subsequently, when the polymeric material is hydrated in solution (e.g., balanced salt solution ("BSS") or other solvents (e.g., water)), the polymeric material swells. The swelling of the polymeric material causes a reduction in the RI. In this manner, the applied energy can be used to vary the RI in the lens in a controlled and predictable manner to create a desired RI profile for the lens.

To form the polymeric body, cross-linking first takes place. This may be referred to herein as "curing," and this can be performed using known techniques. In some embodiments, first and second components are cross-linked to produce a three-dimensional structural random copolymer. Chemical crosslinking can be conducted using a combination of initiators and/or crosslinkers and/or catalysts. Alternatively, crosslinking can be initiated by using Compton electrons indirectly generated in a nuclear irradiator. For example, a cesium 137 or cobalt 60 source can be employed that provides gamma radiation that penetrates into the material of the lens, ionizes the material and generates Compton electrons (i.e., the electrons that are detached during ionization). Both the chemical crosslinking method and the nuclear irradiator crosslinking method provide an environment that results in a uniform crosslinking rate within the reaction region, and thus a homogeneous polymer can be produced.

The copolymer can take the form of a tangled coil in BSS instead of being linear. The random three-dimensional cross-linked coils only form when the intermolecular forces between the copolymer and the solvent molecules are equal to the forces between the solvent molecules, and also equal to the forces between copolymer chain segments. The random three-dimensional crosslinked coils form if, during the polymerization/crosslinking process, a destructive process occurs during the end gelation equilibrating point so that construction and destruction rates become equal. Again, this can be possible with either chemical crosslinking or a radiation process. In the chemical crosslinking process, a combination of initiators and/or crosslinkers and/or catalysts that are promoting crosslinking are matched by the action of an inhibitor. In a radiation process, crosslinking and bond breakage begin to take place at the same rate when the crosslinking density reaches a critical level.

After the polymeric body is formed, ionizing energy is applied to the polymeric body, resulting in the breaking of cross-linked bonds. FIG. 1 conceptually illustrates system 10, which includes ionizing energy source 12, ionizing energy 14, and already-formed (cured) polymeric body 15. Polymeric body 15 may or may not yet have optic surfaces formed thereon. The polymeric body 15 may be mounted in a stable manner and then irradiated using ionizing energy 14. If electron beams are the ionizing energy, electron beam technology as is employed in electron beam lithography for semiconductor manufacture can readily be adapted for use in the methods of the embodiments herein. Electron beam technology enables one to draw custom patterns (direct-write) with sub-10 nm resolution. See, e.g., Altissimo, M., E-beam lithography for micro-/nanofabrication Biomicrofluidics 4, 026503 (2010). Deflection plates 13 are also shown, which are used to create a potential that deflects the beam onto the body 15.

Different system configurations are contemplated. For example, a static lens can be provided, and an electron beam can be provided that can move relative to the static lens to produce a pattern of irradiation. Alternatively, a stationary source may be used and the polymeric body may be adapted to be moved, such as is shown in the optional degrees of freedom illustrated as arrows in FIG. 1. Alternatively, both the source and the lens may be moved.

The pattern of irradiation is defined by electron energy and the direction and position at which electrons hit the lens, and the time for which any position in space is being irradiated. Conversely, a lens adapted to be moved, (e.g., in 6 degrees of freedom as illustrated in FIG. 1) can be provided that is placed in the path of a static electron beam, and moved accordingly with respect to the beam to produce a pattern of irradiation. A configuration in which both the lens and the electron beam are moved can also be employed.

Figure 2:
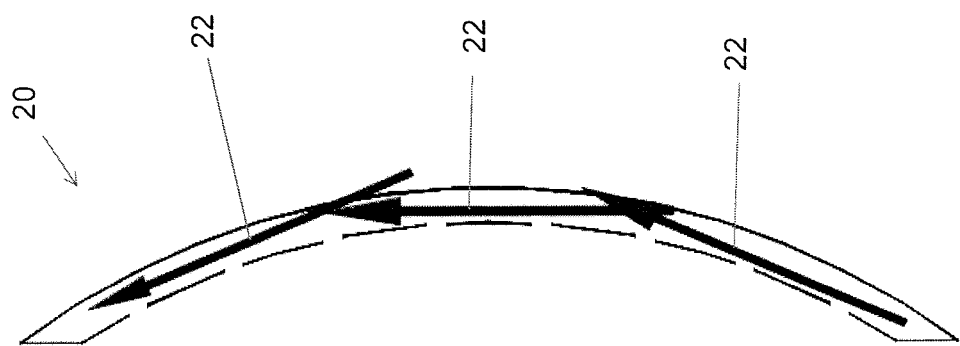
FIG. 2 illustrates an exemplary technique when applying ionizing energy to a lens body.

An exemplary aspect of the method that can be varied to control the resulting RI profile of the lens is the angle of incidence of the electrons. In certain embodiments it is desirable that the electrons hit the lens at glancing angle (e.g., across the whole surface of the lens). This permits a higher energy to advantageously be employed, e.g., in preparing a surface layer. This can be viewed as controlling the amount of absorbed energy or the strength of the electron beam by controlling the angle of incidence. FIG. 2 illustrates this concept, showing lens 20 and energy 22 hitting the lens at glancing (shallow) angles. Lens 20 may be moved relative to the energy source (now shown for simplicity), the energy source may be moved relative to the lens, or both the lens and energy source may be moved.

This application of ionizing energy (e.g., electron beams) differs from the irradiator described above for crosslinking (for forming the polymeric body) in that the ionizing energy in this step is directed in a specific pattern across the lens. Where the beam interacts with the polymeric material, bonds in the polymer backbone are broken, and the refractive index is changed when the polymeric body swells when placed in solution (e.g., BSS, aqueous). The resulting combinations of selected parameters can produce a GRIN in a material that is capable of withstanding steam sterilization (with water inside the material). Different absorbed doses of radiation have a directly proportional effect on the swelling index, and the resulting effect on the polymer system provides the mechanism to form the GRIN.

FIGS. 3A, 3B, 4A and 49 illustrate generally how ionizing energy applied to a polymeric material can increase the amount of swelling when hydrated, and thus result in a greater reduction in RI. FIG. 3A illustrates a formed polymeric material with crosslinks 30 generally indicated as squares (only three are labeled). This may be referred to as a "dry" state. FIG. 3B illustrates the polymeric material when hydrated in solution (e.g., in BSS, magnesium, calcium, etc.). In FIG. 3B the polymeric material has swelled relative to its dry state in FIG. 3A. The positive charges 32 (only three labeled for clarity) repeal each other.

FIG. 4A illustrate a polymeric material after exposure to ionizing energy 40. As can be seen, some crosslinks 42 have been broken due to the exposure to the ionizing energy 41. FIG. 4A, like FIG. 3A, can be referred to as dry state of the polymeric material.

FIG. 4B illustrates the polymer after being hydrated in solution (e.g., in BSS, magnesium, calcium, etc.). As can be seen when comparing FIGS. 3B and 4B, the polymeric material (at least where it was exposed to ionizing energy) swells to a greater extent after ionizing energy absorption compared to no exposure to ionizing energy.

Figure 5:
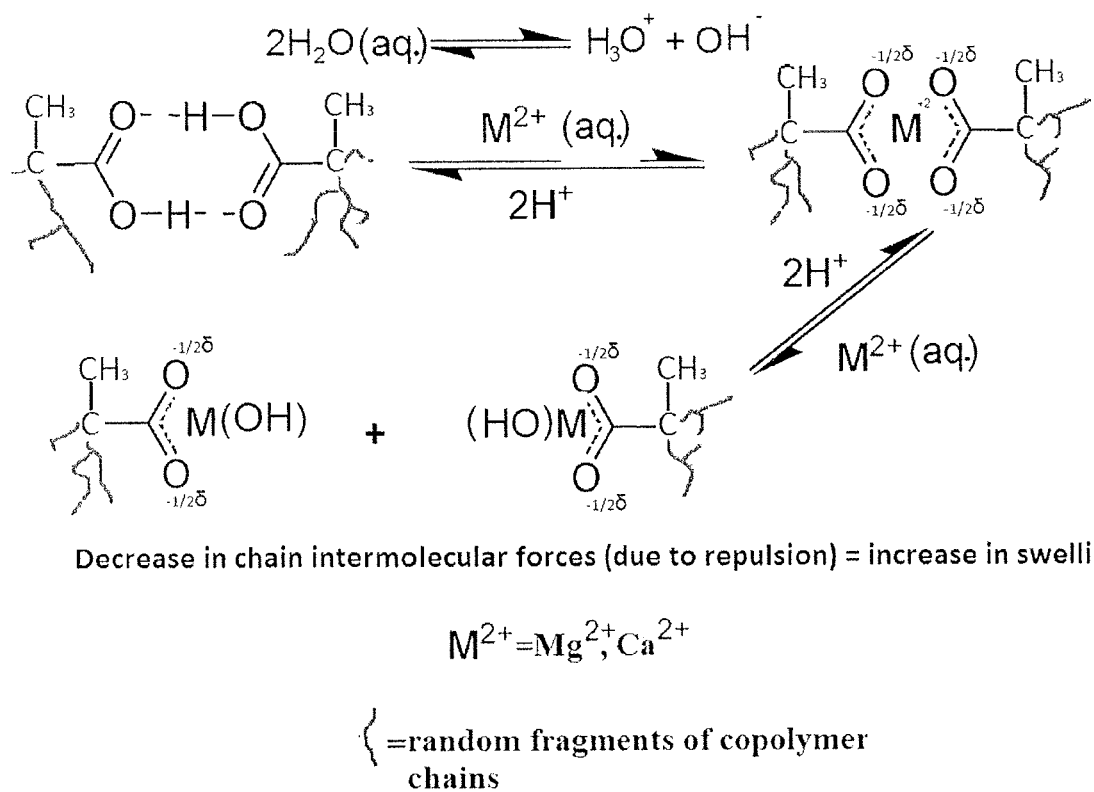
FIG. 5 illustrates in additional detail a manner in which swelling herein may occur.

FIG. 5 illustrates in additional detail the manner in which swelling occurs. In the case of an IOL, the optical properties of the lens when the lens is positioned in the eye are of concern. The copolymer will increase its swell in solution in the presence of calcium and magnesium cations. As $Ca^{2+}$ and $Mg^{2+}$ ions are present inside the material due to diffusion from the solution in which the lens is positioned (e.g., aqueous humor), the swelling variation can be controlled in the lens. Greater swelling indicates more water in the matrix, and therefore a lower refractive index. FIG. 5 illustrates the chemical processes involved for polymethylmethacrylate (PMMA), and can be modified for use with acrylates.

In the top left of the diagram, a pair of hydrogen bonds is shown between two methacrylate groups to indicate a weak crosslink. In the presence of $Ca^{2+}$ and $Mg^{2+}$ ions, there is the potential for stronger complexes to build as the cations bond with the oxygen atoms at the end of the methacrylate groups and create bundles of four or more weakly bonded units. These species are hydrophilic, and thus draw water into the matrix and cause swelling, in turn reducing the refractive index. When high energy electrons are incident upon the polymer, they may break polymer backbone bonds and, according to Flory-Huggins solution theory, cause additional swelling and thus a further decrease in the refractive index. In summary, the initial polymerization produces a hydrophilic polymer that swells in the presence of $Ca^{2+}$ and $Mg^{2+}$ ions. Irradiation with an electron beam (an example of which is shown in FIG. 4A) breaks bonds in this synthetic polymer chain, and allows a change in RI (e.g., RI gradient) to be created. This technique can be used in any of the methods herein (e.g., creating an anti-reflective layer).

The lenses herein, after cross-linking, are generally referred to as being in a dry state. When placed in solution (e.g., BSS, aqueous of the eye), the polymeric material will swell relative to the dry state. The amount of swelling depends on the solution in which the lens is placed. Generally, a lens is packaged for shipping and/or storage, and is then implanted in an eye when ready for use. In some instances the lenses herein can be packaged in BSS (exposure to which causes some degree of swelling of the dry polymeric material), and once implanted they are exposed to aqueous, which may cause slight additional swelling.

Any of the lenses herein can be stored/packaged in a solution such that after implantation, the lenses undergo substantially no additional swelling. This may be beneficial if it is desired that the lens when implanted be as close to the final size as possible. For example, it may be desirable that a lens be implanted in a "full" size so that it is properly stabilized immediately when implanted.

Alternatively, it may be desired to implant a lens in a size that is smaller (i.e., less swelled) than in its final fully implanted size. For example, it may be desirable that an implanted lens be smaller so that it is easier to advance through a delivery tool, after which it expands to a greater extent to its final, implanted, size.

In this manner the degree of swelling post-implantation can be controlled as desired based on the application.

The general methods herein that utilize an electron beam to create a gradient refractive index profile in at least a portion of a lens can also be used to customize a lens to an individual patient. This approach provides a wide variety of possibilities, in that many patient needs can be met by using the techniques herein. A particular patient may benefit from a particular RI profile in the lens. The techniques herein can be tailored as needed to create the particular RI profile in the lens. These properties and others can be provided using the methods of the embodiments, contrary to single refractive index materials where optical properties are determined solely by the morphology of the lens.

While electron beams can advantageously be employed for surface or bulk modification, other energy may also be used, such as X-rays, leptons, protons, positrons, or ionizing radiation from radioactive sources such as from α or β sources.

There are a wide variety of specific applications of the general methods described herein. While some specific examples are provided herein, it is understood that the general methods can be used in other applications to create a desired RI profile for a wide variety of lenses.

One aspect of the disclosure is methods of manufacturing that fabricate lenses, such as intraocular lenses (e.g., IOLs, artificial replacement for the crystalline lens of the eye) with a multi-directional gradient of refractive index (GRIN) that can be controlled in magnitude and in a continuously varying multitude of ways. The GRIN lens material is dimensionally stable through steam sterilization as part of a "wet pack," and is hydrolytically stable during long term use. Since the GRIN of the lens is due to the lens material, with a narrow three-dimensional crosslinking distribution, it is unchanged during long term use. These methods of manufacturing enable lenses to be designed to solve many problems.

For example without limitation, an exemplary application of these methods is the creation of an anti-reflection layer in the lens by producing a thin layer of base material that has had its refractive index lowered. FIG. 6 illustrates an exemplary lens 50 with a thin anti-reflection layer 52 formed therein, with main lens body portion 54.

An anti-reflection layer (i.e., a surface layer) may be useful because it reduces stray light within the eye that can cause dysphotopsia, and it also reduces unwanted reflections in lens applications other than IOLs.

FIGS. 13A and 13B illustrate an additional exemplary lens 100, including optic portion 102 and peripheral support 104. Optic portion 102 includes an aperture 106 (in this embodiment is a central aperture) extending through the optic portion 102. FIG. 13B illustrates region 108 of the optic that forms the aperture that may be irradiated using methods herein to create an anti-reflection layer at the location of the aperture. This may help reduce the scattering of light at the location of the aperture.

The manufacturing processes described herein can be manipulated to form an anti-reflection layer. Generally, electrons having low energy (e.g., 500 eV up to 10 keV) and, optionally, high flux (high rate of flow of electrons through the surface), can be employed for surface modification of a lens. For example, an antireflective layer can be created by, for example, breaking chemical bonds at the surface whereby RI and/or reflectivity is reduced.

To create an antireflective layer, electrons in the range of 0.5 keV to 2 keV can be employed, with an absorbed radiation dose in the range of 4-8 Mrad. The dose may be higher or lower, and can also be dependent on the composition of the irradiated substrate chemical. Alternatively, electrons with an energy of about 0.3 to 1 keV can be used with a high flux. Once the absorbed dose reaches about 8 Mrad, the change in refractive index through the irradiated depth will become substantially uniform and a layer (e.g., layer 52) that has approximately the same refractive index will be created at a 75% relative reduction. By selecting the energy and dose of the electrons appropriately, an interference antireflective layer can be created in the lens material.

Figure 7:
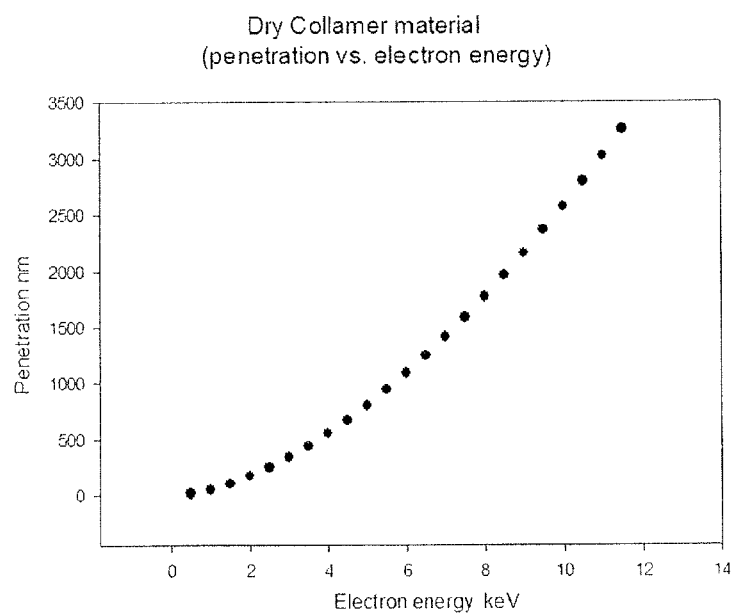
FIG. 7 illustrates how the thickness of a modified surface layer is influenced by the electron energy.

The thickness of a modified surface layer is influenced primarily by the electron energy. This is illustrated in FIG. 7, and is calculated according to the theoretical formula taken from Anderson, C. A., ed., 1973, Microprobe Analysis, John Wiley & Sons, 571 pp.

$$R = \frac{0.064}{\rho E_0}$$

where R is the maximum penetration depth of the electrons in microns, ρ is the density of the material in g/ml and $E_0$ is the energy of electrons upon impact with the surface in keV.

If the change in refractive index is a step, then the desired thickness is one quarter of the wavelength of light in the modified surface layer, which is reduced from the wavelength in air by a factor equal to the RI. Accordingly, the layer will be about 100 to 200 nm in thickness. Using a single electron energy, the actual RI change is an exponential decay. As such, the thickness in some embodiments may be somewhat smaller or larger than from about 100 to 200 nm, e.g., from about 50 to 400 nm, wherein the thickness is defined as 1/e of the maximum RI change. In some embodiments the thickness is 0.1 microns to 10 microns. In some embodiments the thickness is 1 micron to 10 micron. A more step-like layer can be created by varying the electron energy during exposure. Moreover, the angle of incidence of light onto the lens's curved surface can be taken into consideration by varying the thickness of the surface layer as a function of the distance from the center of the lens.

Figure 8:
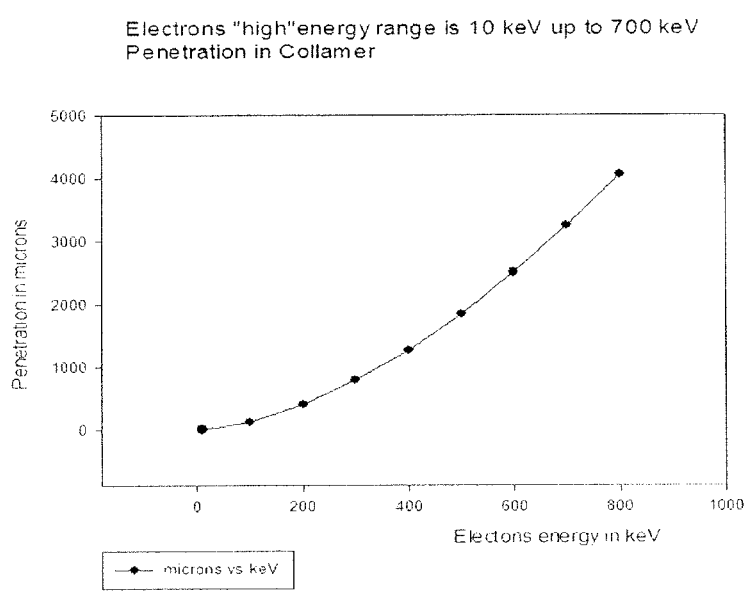
FIG. 8 illustrates the relatively higher energy range for beta radiation, compared to FIG. 7.

While the disclosure herein mainly describes electron beams as the ionizing energy, other types of ionizing energy, such as beta radiation, may be used. However, beta radiation is typically of higher energy (e.g., $^{90}Sr \rightarrow ^{90}Y$ at 546 keV) and its use can be limited by the thickness of the layer desired or, for applications other than anti-reflection layers, by the thickness of the lens itself. For an IOL, this thickness is between 0.05 mm and 5 mm. Also, the energy of beta radiation cannot be tuned, unlike electron radiation. When compared to the electron radiation graph shown in FIG. 7, FIG. 8 illustrates the relatively higher energy range for beta radiation.

An additional exemplary application is to create lenses that focus light from a wide range of distances without moving or changing shape whereby light entering the lens from different directions and incident on different surface positions on the lens will experience optical pathways through the lens that differ due to RI variations throughout the lens. Focusing light from a wide range of distances is useful to patients fitted with the lens, as IOLs do not typically provide accommodation similar to that provided by the native crystalline lens. Additionally, the technology can be useful in other lens applications, such as camera lenses designed with a large depth of field.

Figure 9:
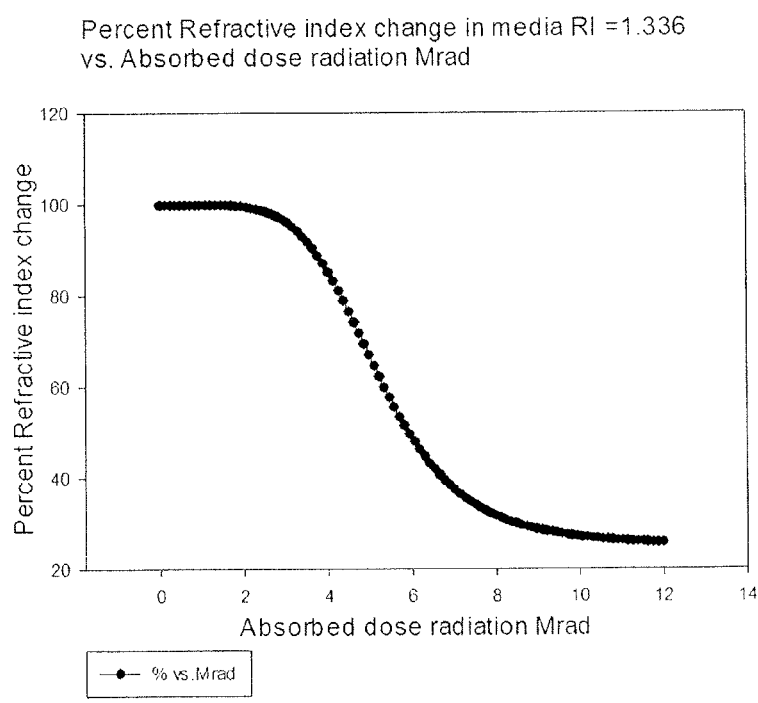
FIG. 9 shows the percentage change in refractive index, wherein 100% refers to a surface RI unchanged from the bulk and 0% refers to the surface RI being reduced to the RI of the solution in which it is held.

The change in refractive index for the surface lens material relative to the bulk lens material depends on the absorbed radiation dose. FIG. 9 shows the percentage change in refractive index, wherein 100% refers to a surface RI unchanged from the bulk and 0% refers to the surface RI being reduced to the RI of the solution in which it is held (e.g., a balanced salt solution in packaging, aqueous humor in the eye).

Another exemplary application of the general technique described herein is creating an extended surface layer over a thickness of several wavelengths that does not cause destructive interference of light reflected from both surfaces. This can be represented by FIG. 6, but region 52 would be a gradient RI rather than a layer with a uniform RI. In this exemplary method, the RI of the outer surface of the material is reduced to match as closely as possible (e.g., 10% or less variance, such as 5% or less variance) the RI of aqueous humor. The small change in RI between the lens and aqueous humor results in less reflection. According to Fresnel's equations the proportion of reflected power for normal incidence light $$= \frac{(n_l - n_a)^2}{(n_l + n_a)^2}$$

where $n_l$ is the refractive index of the lens and $n_a$ is the refractive index of aqueous humor. This method utilizes a surface dose of about 8 Mrad or more but layers directly below the surface receive less radiation thus creating a gradual variation in refractive index. The time required to create such a gradient must therefore be selected to prevent saturation as described above. Achieving the thicker surface layer requires higher energy electrons in the range of 1 keV to 10 keV, but still in the range of "low" energy as defined herein.

Multiple directional incidence angles of irradiation can be used to create different three-dimensional (3D) patterns of the gradient refractive index in the bulk of the lens, or on the surface of the lens, or both. Regardless of orientation, the change in RI is determined by electron energy (penetration) and absorbed dose (magnitude of effect), such that different patterns can be achieved by varying the lens-beam orientation. Predictions of the effect can be made by calculating, for all the positions in the 3D matrix, how deep the position is within the lens relative to the direction of the electron beam and the absorbed dose at that position, and integrating over time as the beam is moved.

The aforementioned methodology is particularly useful in the surface modification of a lens, examples of which have been described herein. When modification of the bulk of the lens (i.e., more than just the surface) is desired, however, high energy (e.g., from 10 keV to 700 keV, inclusive) electrons can be employed for penetration deeper into the bulk of the lens. The energy of the beam can thus be modified as needed to penetrate to the depth(s) desired for a particular application. By adjusting the energy profile and flux of the electrons, as well as the angle of incidence and location of irradiation, a desired RI profile throughout any portion of the lens can be achieved.

Figure 10:
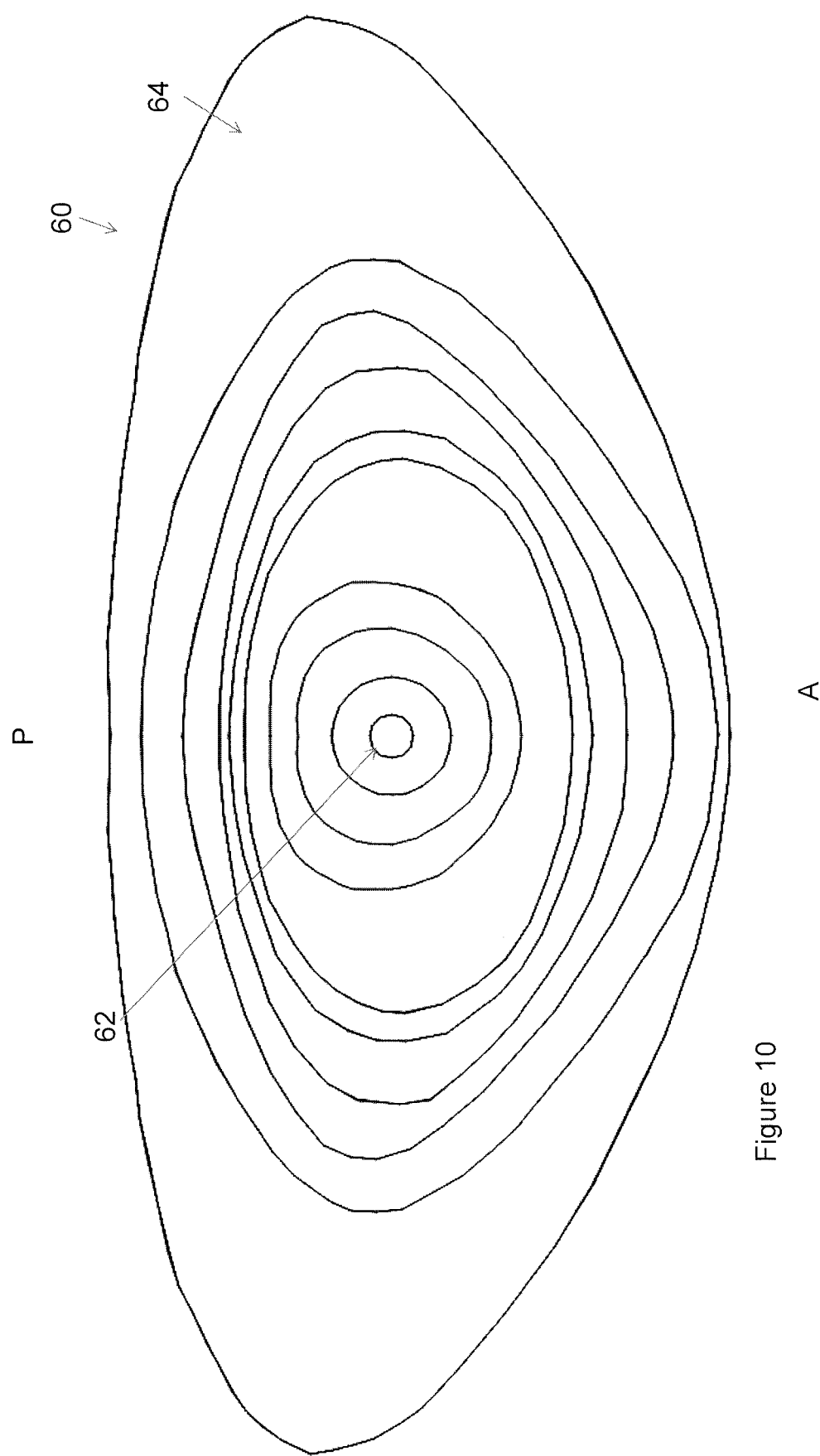
FIG. 10 is an exemplary lens that can have a refractive index distribution substantially the same as a native crystalline lens.

Generally, retinal images that are similar to those provided by the natural crystalline lens may be advantageous to the lens recipient, as the brain has grown accustomed to such images and the brain's neural networks may better be able to process such images. An additional exemplary application of the methods herein is to create a lens that produces images that are more similar to those produced by the natural crystalline lens. FIG. 10 illustrates exemplary lens 60 that can be created using methods herein. Lens 60 is created to function like the natural crystalline lens, with a gradually changing RI as indicated by the internal lines that represent refractive index contours in the figure. Lens 60 may be implanted in a capsular bag to replace a removed native crystalline lens. In FIG. 10, anterior is towards the bottom of the page, and posterior is towards the top of the page. The RI varies in the lens body, with the RI being greater in central region 62 than in outer region 64. Lens 60 is an example of an optic body that has a three-dimensional polymeric matrix with a refractive index distribution substantially the same as a refractive index distribution of a natural crystalline lens. Lens 60 is also an example of an optic body that has a shape that is substantially the same as a shape of a natural crystalline lens. One of skill in the art will understand that the comparison to a native crystalline lens (for which there may be some subject to subject variability) does not render this description indefinite or vague, since one of ordinary skill in the art will understand what is meant by a refractive index distribution substantially the same as a refractive index distribution of a natural crystalline lens, as well as a shape that is substantially the same as a natural crystalline lens.

The lens 60 in FIG. 10 is an example of a lens that can be adapted so that it swells to a final implanted state (size) after implantation. For example, it may be desirable that lens 60 have a smaller delivery size to ease the delivery through a lens inserter, then swell (expand) to a greater state once inserted so that it is better secured within the eye (e.g., within a capsular bag).

Figure 11:
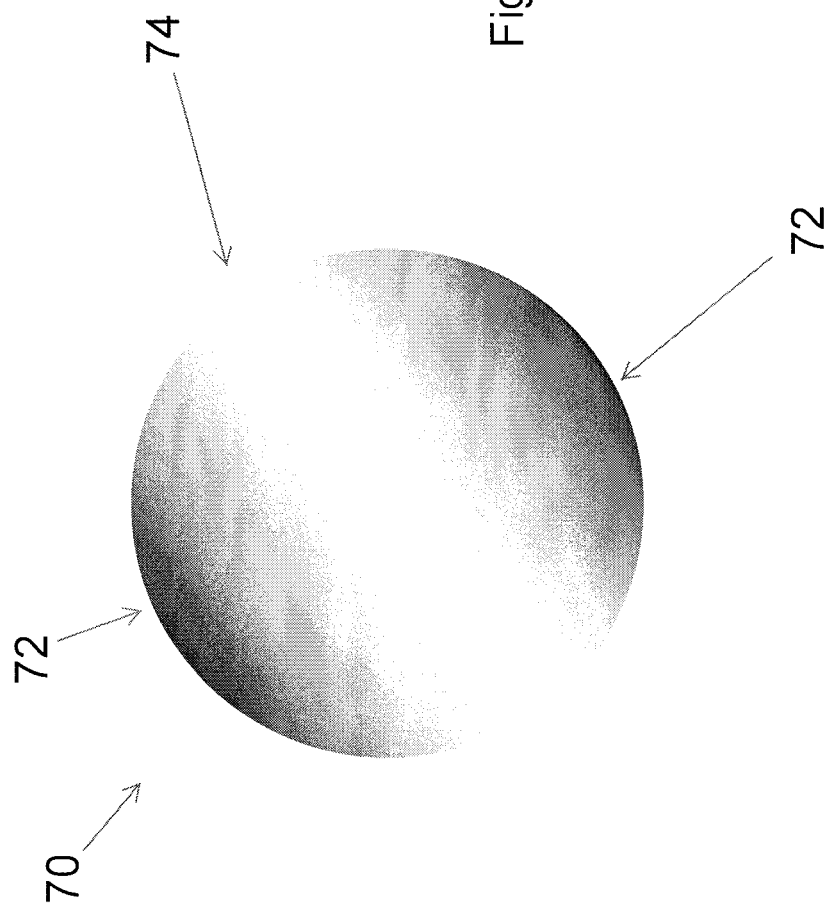
FIG. 11 illustrates an exemplary optic body with a varying RI in the optic body that can be created using the methods herein.

FIG. 11 illustrates an alternative optic body 70 with a varying RI in the optic body that can be created using the methods herein. Optic body 70 can be incorporated into any suitable ophthalmic lens (e.g., an IOL with one or more haptics). Ionizing energy can be applied to a polymeric body to create optic body 70. Region 74 may be considered a lower RI region compared to regions 72. The RI may vary continuously (gradient) through the lens 70. Lens 70 is an example of a lens that is configured to treat ametropia (via a spherical component of the lens shape) and astigmatism (via a cylindrical component of the lens shape). The degree of change in RI between regions 72 and 74 can be any suitable degree.

A further embodiment of the methods described herein is the creation of an embedded Fresnel lens within a conventionally shaped lens, e.g., a bi-convex lens or a bi-concave lens. To create optical power, lens surfaces need to be curved. In the case of a biconvex lens this means that the center has to have a central thickness that increases with optical power and for a biconcave lens the edge thickness that increases with optical power. A Fresnel lens has a shape that segments the curvatures into different sectors thus reducing the thickness of the lens. One disadvantage of a Fresnel lens is that it can have sharply changing curvatures that can scatter light. By producing the Fresnel lens within a conventionally shaped lens, some of the power can come from the outer shape of the conventional lens and more power can be obtained by replicating a Fresnel lens within the conventional lens by creating curved zones of increased power. Furthermore, Fresnel lenses can be designed to have more than one focus to provide simultaneously, for instance, good focus at far distance and near, or good focus at far distance and near and an intermediate distance. Furthermore, the interaction between the different refractive zones of the Fresnel lens can create beneficial diffractive effects and control of the exact shape of the refractive zones can reduce scatter and create better images.

One aspect of this disclosure is a copolymer material or a combination of copolymer materials that can be used to make a GRIN lens. The lens can be incorporated into, e.g., an IOL. Properties of IOL materials include high elasticity to allow ease of insertion into the eye, low reflectivity to avoid dysphotopsia, good biocompatibility does not leech toxic materials into the eye), and be mechanically capable of accurately holding a stable shape that is composed of a lens and supporting elements without disturbing or irritating the existing structure of the eye.

Some ophthalmic devices may include one or more peripheral supports (e.g., one or more haptics, such as plate haptics or arm haptics) that extend radially outward from an optic, and provide support to the optic when placed in an eye. Any of the methods of irradiating herein may occur after the optic and any peripheral support(s) have been formed into an integral structure (e.g. via lathing, molding, machining, or any combination thereof).

The methods of creating non-uniform cross-link densities herein may also be used on non-optic body portions (e.g., one or more haptics) of a lens. At least a portion of the non-optic body portion may also be irradiated to create a varying refractive index. This may be helpful to reduce light scattering in some subjects who have relatively larger pupils, where more light passes through the non-optic portion due to the larger pupil size. All of the methods of irradiating and swelling described herein may thus also be used on a non-optic portion of a lens, as well as on an optic body.

Exemplary Method of Preparing a Gradient Refractive Index in a Three-Dimensional Copolymer The copolymer system of certain embodiments is composed of a large proportion of a non-ionic acrylic monomer and a small proportion of an ionic monomer such as an organic acid. The term "organic acid" encompasses acids made up of molecules containing organic radicals ((hydro) carbon containing moieties). Such acids include, for example, acrylic acid, formic acid (H—COOH), acetic acid ($CH_3COOH$) and citric acid ($C_6H_8O_7$), each of which contain the ionizable —COOH group. The term "acrylic" as applied to monomers includes synthetic plastic resins derived from acrylic acids. The present hydrophilic monomers and hydrophobic monomers must be selected such that the hydrophobic monomer(s) is soluble in the hydrophilic monomer(s). The hydrophilic monomer acts as a solvent for the hydrophobic monomer. Suitable monomers can be readily selected by those of ordinary skill in the art to which the present disclosure pertains. Examples of suitable acrylic monomers, include 4-methacryloxy-2-hydroxybenzophenone, ethyl-3-benzoil acrylate, N-propyl methacrylate) N-propyl methacrylate (acrylic), ethyl-methacrylate, methyl methacrylate, n-heptyl methacrylate, 2-hydroxyethyl methacrylate (HEMA), hydroxypropyl methacrylate, 2-hydroxyethyl methacrylate, hydroxypropyl methacrylate poly(ethylene glycol)n monomethacrylate, 4-hydroxybutyl methacrylate, and other monomers as are known in the art. It is generally observed that swelling in water is reduced when sodium chloride or other salts are present in the copolymer system. The targeted amount of swelling can therefore be modified by manipulating salt content within the copolymer system when the lens is outside of the eye. The lens can expand more or less once implanted in the eye when exposed to aqueous, depending on the solution in which it is placed prior to implantation.

Gradient Refractive Index in a Three-Dimensional Collagen-Containing Copolymer

Copolymers can be modified by adding collagen or a similar biological molecule to the polymer, in which case the radiation method can be employed. This formulation method provides the structural and dimensional characteristics of the resulting material from which an IOL with GRIN can be produced. Any type of collagen from any source can be employed. Suitable collagen materials include, but are not limited to, collagen obtained from pig's eye sclera or cornea, or fibroblasts (e.g., artificially produced or cultured from genetically modified yeast, etc.). The collagen is a naturally stable polyenic, which comprises hydrophobic, hydroxylic and polarized amino-acids, e.g., telo-collagen. Copolymeric materials comprising collagen materials are described in U.S. Pat. Nos. 5,654,349, 5,910,537, 5,661,218. Collamer can be desirable in certain embodiments due to its stability to radiation. Hydrogels are associated with calcification (hydroxyapatite deposition). Biological molecules such as denatured collagen, when incorporated into the lens, can attract fibronectin, forming a protective layer. This protective layer of fibronectin (unique to an individual patient) is not recognized as a foreign body, thereby reducing the susceptibility of the lens to calcification. Accordingly, providing materials that are radiologically resistant and biologically active as components of the lens can yield a lens having superior stability, in particular to optical degradation, and biocompatibility.

Forming a polymeric body may include mixing a nonionic acrylic monomer with the ionic monomer (e.g., an acid such as formic acid). The weight ratio of nonionic acrylic monomer to ionic monomer can be in the range of about 10:1 to about 10,000:1, e.g., 50:1 to 200:1, e.g., 75:1, 100:1, 125:1, 150:1, or 175:1. Additional steps in an exemplary method of preparing an exemplary material may be described in U.S. App. No. 62/765,088, whose priority is claimed herein, and the disclosure of which is incorporated by reference herein for all purposes.

Accordingly, once the polymer is formed, an IOL (or other lens) can be manufactured in a traditional manner using, for example, a lathe and null or with a mold, and can then be modified using a second irradiation process.

The change in RI as a function of radiation absorbed is influenced by factors, such as the concentration of anionic components, such as methacrylic acid and acrylic acid, which are crosslinked into the copolymer. The concentration of the anionic components influence the swell factor, which in turn influences RI. More swelling correlates with a lower RI, and a higher concentration of the anionic components results in more swelling (and thus lower RI). The concentration of bi-cations in physiological and BSS ranges are as follows: magnesium 0.7-2.0 mmol/L and calcium 1-3.5 mmol/L. The propensity for the material to swell is determined by anionic components, such as methacrylic acid and acrylic acid, that are crosslinked into the copolymer. Excess monomers are typically removed during the extraction process.

The ratios of the two different monomers within the copolymer structure, the absorbed dose, and the electron energy can be varied within moderate ranges to achieve different balances of properties within the resulting GRIN lens. In this way, a desired. RI profile can be created in the lens. As an example, the optical aberrations of a patient's visual system can be measured using a device such as a wavefront aberrometer and the required lens correcting for the aberrations can be calculated. Thereafter, a three-dimensional irradiation plan can be developed whereby the dose at any point in the lens, as a function of electron energy, can be calculated and an irradiation plan, consisting of beam position and angle, electron flux and electron energy, can be produced. Lenses for different patients can be produced from one single design of a single refractive index lens or the geometrical properties of the lens can be used as additional degrees of freedom (design parameters). There is thus great flexibility in how the methods herein can be used to create a wide variety of lenses based on the desired refractive index profile.

The following references relate to use of lasers to modify refractive index of lenses: U.S. Pat. Nos. 9,545,340; 9,492,323; 9,144,491; 9,060,847; 8,932,352; 8,901,190; 8,617,147; 8,512,320; 8,486,055; 8,337,553; and 7,789,910, all of which are incorporated by reference herein.

EXAMPLES

Figure 12:
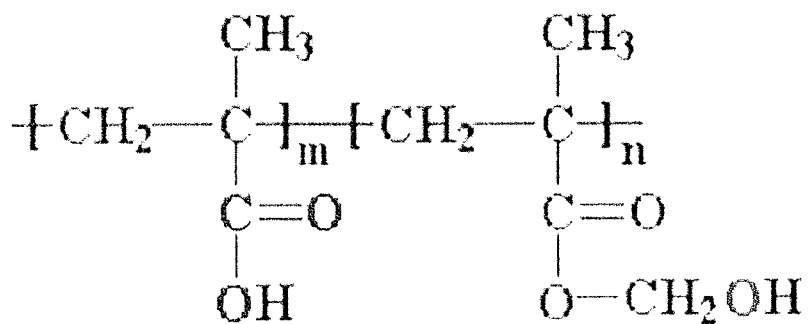
FIG. 12 shows a portion of a polymer chain with the acrylic acid side group (left) and methacrylate side group (right).

An exemplary polymer may be a structural copolymer produced from hydroxyethylmethacrylate monomers as a major component and acrylic acid as a minor component. The weight ratio may be as indicated above. FIG. 12 shows such a portion of a polymer chain with the acrylic acid side group (left) and methacrylate side group (right). The copolymer is produced either chemically or during nuclear irradiation (described above), and then amended using the electron beam irradiation methods (or other ionizing energy source) described herein to create the GRIN lens.

Following the generalized formula presented above, other copolymer combinations can be used to achieve the same final properties. An absorbed dose radiation sensitive refractive index changing copolymer composition comprising a methacrylic ionic monomer and a methacrylic nonionic monomer that is sensitive to electron beam bombardment can be employed in preparing materials with varying refractive index that are also compatible with use in the eye.

The term "low energy" as used herein is a broad term, and refers without limitation to 500 eV to 10 keV, inclusive.

The term "high energy" as used herein is a broad term, and refers without limitation to 10 keV to 700 keV, inclusive.

The description herein and examples illustrate exemplary embodiments of the present disclosure in detail. Those of skill in the art will recognize that there are numerous variations and modifications of the inventions herein that are encompassed by its scope. Accordingly, the description of exemplary embodiments should not be deemed to limit the scope of the inventions herein.

The illustrative embodiments described in the detailed description, drawings, and claims are not meant to be limiting. The teachings herein can be applied in a multitude of different ways, including for example, as defined and covered by the claims. It should be apparent that the aspects herein may be embodied in a wide variety of forms and that any specific structure, function, or both being disclosed herein is merely representative. Based on the teachings herein one skilled in the art should appreciate that an aspect disclosed herein may be implemented independently of any other aspect and that two or more of these aspects may be combined in various ways. For example, a system or apparatus may be implemented or a method may be practiced by one of skill in the art using any reasonable number or combination of the aspects set forth herein. In addition, such a system or apparatus may be implemented, or such a method may be practiced using other structure, functionality, or structure and functionality in addition to or other than one or more of the aspects set forth herein. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, and designed in a wide variety of different configurations, all of which are explicitly contemplated and made part of this disclosure. It is to be understood that the disclosed embodiments are not limited to the examples described below, as other embodiments may fall within the disclosure and the claims.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Where a range of values is provided, it is understood that the upper and lower limit, and each intervening value between the upper and lower limit of the range is encompassed within the embodiments.

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

What is claimed is:

1. An intraocular lens (IOL), comprising:
an optic body made from a three-dimensional polymeric matrix comprising a copolymer system comprising at least one non-ionic acrylic monomer,
wherein the three-dimensional polymeric matrix has a non-uniform cross-link density, wherein the non-uniform crosslink density of the matrix is adapted to create an anti-reflection surface layer in the optic body when the optic body is exposed to aqueous humor in an eye,
wherein the anti-reflection surface layer comprises a region of the matrix that is 50 nm to 100 microns thick,
wherein the anti-reflection surface layer is at least partially disposed around a central aperture formed in the optic body, wherein said anti-reflection surface layer has been formed by irradiating the three-dimensional polymeric matrix with ionizing energy in a pattern configured to create said non-uniform cross-link density within the matrix.

2. The lens of claim 1, wherein the three-dimensional polymeric matrix that has a non-uniform cross-link density includes a first region with fewer cross links than a second region.

3. The lens of claim 2, wherein the first region and the second region are within a gradient of cross-link density.

4. The lens of claim 2, wherein the first region is in a first layer with a first cross-link density, and the second region is in a second layer with a second cross-link density.

5. The lens of claim 2, wherein the anti-reflection surface layer comprises the first layer.

6. The lens of claim 1, wherein the entire optic body does not have a gradient cross-link density.

7. The lens of claim 1, wherein the copolymer system further comprises at least one ionic monomer.

8. The lens of claim 7, wherein the weight ratio of a first one of the at least one non-ionic acrylic monomer to a first one of the at least one ionic monomer is 10:1 to 10,000:1, such as 50:1 to 200:1, such as 75:1 to 175:1, such as 75:1, 100:1, 125:1, 150:1, or 175:1.

9. The lens of claim 7, wherein the at least one ionic monomer comprises hydroxyethylmethacrylate.

10. The lens of claim 1, wherein the copolymer system further comprises a collagen material.

11. The lens of claim 1, wherein the optic body is an optic body of a phakic IOL.

12. The lens of claim 1, further comprising a hydrating solution to which the optic body is exposed, wherein the non-uniform cross-link density causes the three-dimensional polymeric matrix to swell in a non-uniform manner when hydrated in the solution, thereby creating a non-uniform refractive index within the optic body.

13. The lens of claim 12, wherein the hydrating solution is a balanced salt solution.

14. The lens of claim 12, wherein the hydrating solution includes constituent parts such that when the lens is exposed to aqueous humor in an eye, the amount of swelling in the three-dimensional polymeric matrix will not substantially change.

15. The lens of claim 12, wherein the hydrating solution includes at least one of magnesium ions or calcium ions.

16. The lens of claim 12, wherein the non-uniform refractive index includes first and second discrete layers having first and second refractive indices, respectively.

17. The lens of claim 12, wherein the non-uniform cross-link density includes a gradient cross-link density.

* * * * *